United States Patent [19]

Kennedy

[11] Patent Number: 5,420,768
[45] Date of Patent: May 30, 1995

[54] PORTABLE LED PHOTOCURING DEVICE

[76] Inventor: John Kennedy, 23 Mollison Court, Guelph, Ontario, Canada, N1C 1A7

[21] Appl. No.: 119,571

[22] Filed: Sep. 13, 1993

[51] Int. Cl.6 .............................................. B25B 33/00
[52] U.S. Cl. .................... 362/119; 362/109; 362/234; 362/184; 362/800
[58] Field of Search ............... 362/109, 119, 420, 234, 362/184, 295, 800, 32, 202; 433/29, 215, 229

[56] References Cited

U.S. PATENT DOCUMENTS

| | | | |
|---|---|---|---|
| 3,638,013 | 1/1972 | Keller | 362/120 X |
| 4,230,453 | 10/1980 | Reimers | 362/119 X |
| 4,385,344 | 5/1983 | Gonser | 362/293 X |
| 4,666,406 | 5/1987 | Kanca, III | 433/229 |
| 4,729,076 | 3/1988 | Masami et al. | 362/800 X |
| 4,963,798 | 10/1990 | McDermott | 362/800 X |
| 5,003,434 | 3/1991 | Gonser et al. | 362/119 X |
| 5,150,016 | 9/1992 | Sawase et al. | 362/800 X |
| 5,161,879 | 11/1972 | McDermott | 362/800 X |

*Primary Examiner*—Ira S. Lazarus
*Assistant Examiner*—Thomas M. Sember
*Attorney, Agent, or Firm*—David W. Wong

[57] ABSTRACT

The portable photocuring device has a light emission diodes matrix which can be energized with battery power to provide optical power for photocuring curing purposes. The diodes can be easily controlled and adjusted to emit light of selected colors and intensity with complex instrumentation.

4 Claims, 1 Drawing Sheet

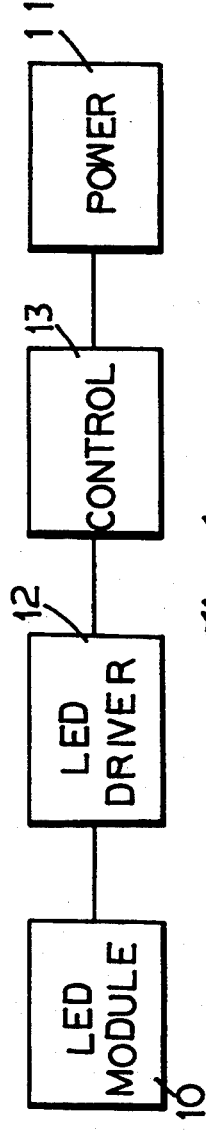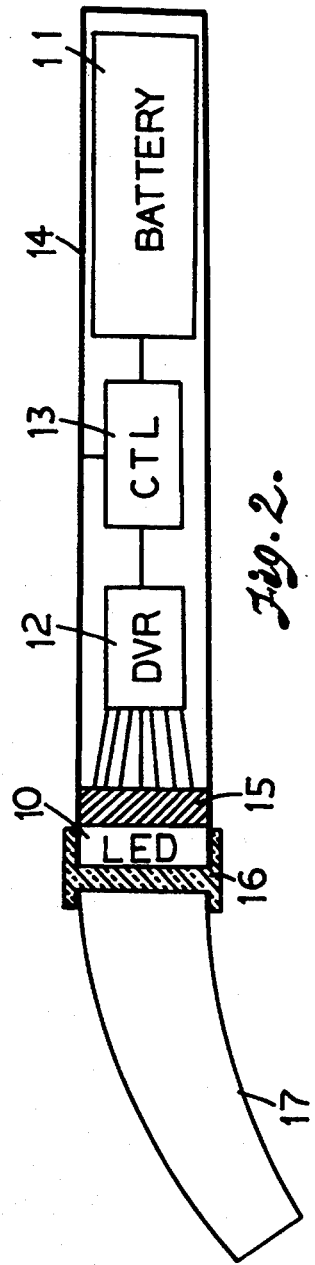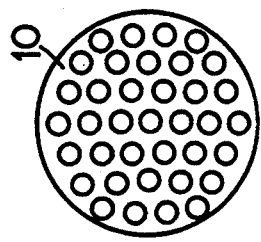

PORTABLE LED PHOTOCURING DEVICE

BACKGROUND OF THE INVENTION

This invention relates to photocuring curing device, and particularly relates to a portable photocuring curing device suitable for dental curing purposes.

Commonly, the radiant energy required for photocuring is provided by a halogen lamp located in a power station or inside a portable photocuring device. The light thus generated by the halogen lamp can be conveyed and directed to the location for curing with a conventional light guide made of a plurality of optical fibres. Due to the large amount of inherent heat also generated in the halogen lamp, it is necessary to provide a large blower to dissipate the heat during operation. Such large blower requires a relatively large size housing and would thus increase the housing size of the light generating means. For this reason the halogen lamp light source device tends to be relatively bulky and large in size. Also, halogen lamp has a relatively short life span and the quality of the light generated by the lamp would decline with the deterioration of the lamp. Thus the light becomes less efficient. Furthermore, the colour of the light generated by the halogen lamp may only be changed with the use of colour filters.

SUMMARY OF THE INVENTION

It is the principal object of the present to provide a photocuring device using light emitting diodes as the light generating means.

It is another object of the present invention to provide a photocuring device using a semiconductor module having a plurality of light emitting diodes formed therein.

It is another object of the present invention to provide a portable hand-held photocuring device having a relatively small size and light in weight.

It is yet another object of the present invention to provide a portable photocuring device in which the colour of the light generated therein can be easily controlled without the use of colour filters.

It is still another object of the present invention to provide a portable photocuring device which is simple in construction.

Briefly, the photocuring device comprises a light emitting module having a plurality of light emitting semiconductor means formed therein. A power means is coupled to the semiconductor means and is operative to provide the electrical power for energizing the semiconductor means to emit light energy of a selected level. A control means is connected to the semiconductor means and the power means and is operative to vary the light energy emitted from the semiconductor means. The entire system can be enclosed in a relatively small housing that can be held in a user's palm.

DESCRIPTION OF THE DRAWINGS

Other objects and advantages of the present invention will become apparent from the following detailed description of the preferred embodiments thereof in connection with the accompanying drawings, in which FIG. 1 is a schematic block diagram of the circuit system of the present invention.

FIG. 2 is a front elevation view of the light emission diode module thereof.

FIG. 3 is a side sectional view of the portable photocuring device according to the present invention.

DETAILED DESCRIPTION OF THE PREFERRED EMBODIMENTS

With reference to the drawings in which like reference numerals in the various views indicate same parts, the light emitting diodes module 10 is made of a semiconductor matrix having a plurality of light emitting diodes formed on a ceramic substrate. A large number of light emitting diodes can be typically formed on a substrate of only 3 mil in diameter. The light emitting diodes commonly abbreviated as LEDs can be actuated by a power source 11 such as a rechargeable battery through a driver circuit 12 and a control circuit 13. The light emitted by the LEDs may have a peak wavelength of 470 nm which can be used for photocuring purposes. LEDs of various selected colours may be formed on the module by using selected colour dyes so that the emitted light is a pure white light or a combination of a selected colour lights to provide a predetermined photocuring effect.

The driver circuit 12 may provide a series of pulse signals for actuating the LEDs to emit the light in a series of short durations such that relatively little heat is generated by the LEDs.

The entire photocuring system of the present invention can be enclosed particularly in a relatively small housing that can be conveniently held in a user's palm, as best shown in FIG. 3. The LED module 10 is mounted at the front end of the housing 14. A heat sink 15 such as an aluminum block is located juxtaposed to the LED module 10 so as to dissipate any heat that may be generated in the LEDs during operation. The light emitting front surface of the LED module 10 is covered with a transparent protective cap 16 mounted to the front end of the housing such that the LEDs will not be contaminated with dust; and the cap 16 can be cleaned without causing any physical damage to the LEDs. The front portion of the cap 16 is also shaped or provided with mounting means for receiving a light guide 17 removably mounted thereto. The light guide 17 transmits the light emitted from the LED module to the location for photocuring. It can be appreciated that due to the simple construction and the small physical size of the device, it is very light in weight and is easy to operate. The LEDs have a very long life span.

While the instant invention has been shown and described in what is considered to be a practical and preferred embodiment, departures may be made within the spirit and scope of this invention which should therefore not be limited except as set forth in the claims which follow and within the doctrine of equivalents.

What is claimed is:

1. A hand-held portable photocuring device comprising,
   a portable housing having a front end and rear end,
   a light emitting semiconducting means having a matrix of a plurality of light emitting diode means mounted at said front end, said light emitting diode means being operative to emit in combination a light energy suitable for photocuring,
   a power means coupled to said semiconducting means and operative to provide the electrical power for energizing said plurality of light emitting diode means to emit in combination said light energy, control means connected to said semiconducting means and said power means, and operative to vary the level of said light energy, a mounting means provided at said front end of said housing, a tubular light guide member mounted to said mounting means, said light guide member being operative to direct said light energy generated from said light emitting diode means to a photocuring location disposed adjacent to a distal free end of said light guide member, a transparent cap member mounted at said front end and covering over said light emitting diode means, a heat sink means disposed juxtaposed to said semiconducting means and being operative to dissipate heat generated in said semiconducting means.

2. A hand-held portable photocuring device according to claim 1 wherein said light emitting diode means is capable of emitting light energy having a level of at lest 470 nanometers.

3. A hand-held portable photocuring device according to claim 2 wherein said light guide means is removably mounted to said mounting means.

4. A hand-held portable photocuring device according to claim 3 including a driver means connected to said semiconducting means and said control means and being operative to actuate said light emitting diode means to generate said light energy, and said power means is a rechargeable battery disposed in said housing.

* * * * *